(12) United States Patent
Novikov et al.

(10) Patent No.: US 11,727,573 B2
(45) Date of Patent: Aug. 15, 2023

(54) SEQUENTIAL SEGMENTATION OF ANATOMICAL STRUCTURES IN 3D SCANS

(71) Applicants: Agfa Healthcare NV, Mortsel (BE); Vrvis Zentrum Fur Virtual Reality Und Visualisierung Forschungs-GmbH, Vienna (AT)

(72) Inventors: Alexey Novikov, Mortsel (BE); David Major, Mortsel (BE); Maria Wimmer, Mortsel (BE); Dimitrios Lenis, Mortsel (BE); Katja Buehler, Mortsel (BE)

(73) Assignees: Agfa Healthcare NV, Mortsel (BE); VRVis Zentrum fur Virtual Reality und Visualisierung Forschungs-GmbH, Vienna (AT)

( * ) Notice: Subject to any disclaimer, the term of this patent is extended or adjusted under 35 U.S.C. 154(b) by 358 days.

(21) Appl. No.: 16/972,791

(22) PCT Filed: May 28, 2019

(86) PCT No.: PCT/EP2019/063745
§ 371 (c)(1),
(2) Date: Dec. 7, 2020

(87) PCT Pub. No.: WO2019/233812
PCT Pub. Date: Dec. 12, 2019

(65) Prior Publication Data
US 2021/0248749 A1 Aug. 12, 2021

(30) Foreign Application Priority Data
Jun. 7, 2018 (EP) .................................... 18176521

(51) Int. Cl.
*G06T 7/00* (2017.01)
*G06T 7/11* (2017.01)
(Continued)

(52) U.S. Cl.
CPC .................. *G06T 7/11* (2017.01); *G06N 3/08* (2013.01); *G16H 30/20* (2018.01);
(Continued)

(58) Field of Classification Search
CPC .................. G06T 7/11; G06T 2200/04; G06T 2207/20081; G06T 2207/20084;
(Continued)

(56) References Cited

U.S. PATENT DOCUMENTS

2018/0240235 A1* 8/2018 Mazo ........................ G06T 7/11
2018/0260951 A1* 9/2018 Yang ...................... G06N 3/084
(Continued)

OTHER PUBLICATIONS

Chen Yani et al, "Accurate and Consistent Hippocampus Segmentation Through Convolutional LSTM and View Ensemble", International Workshop on Machine Learning in Medical Imaging, Sep. 7, 2017, pp. 88-96, Lecture Notes in Computer Science vol. 10541, Springer, Cham. (Year: 2017).*

(Continued)

*Primary Examiner* — Van D Huynh
(74) *Attorney, Agent, or Firm* — Leydig, Voit & Mayer, Ltd.

(57) ABSTRACT

Method of segmenting anatomical structures such as organs in 3D scans in an architecture that combines U-net, time-distributed convolutions and bidirectional convolutional LSTM.

20 Claims, 3 Drawing Sheets

Figure 1:
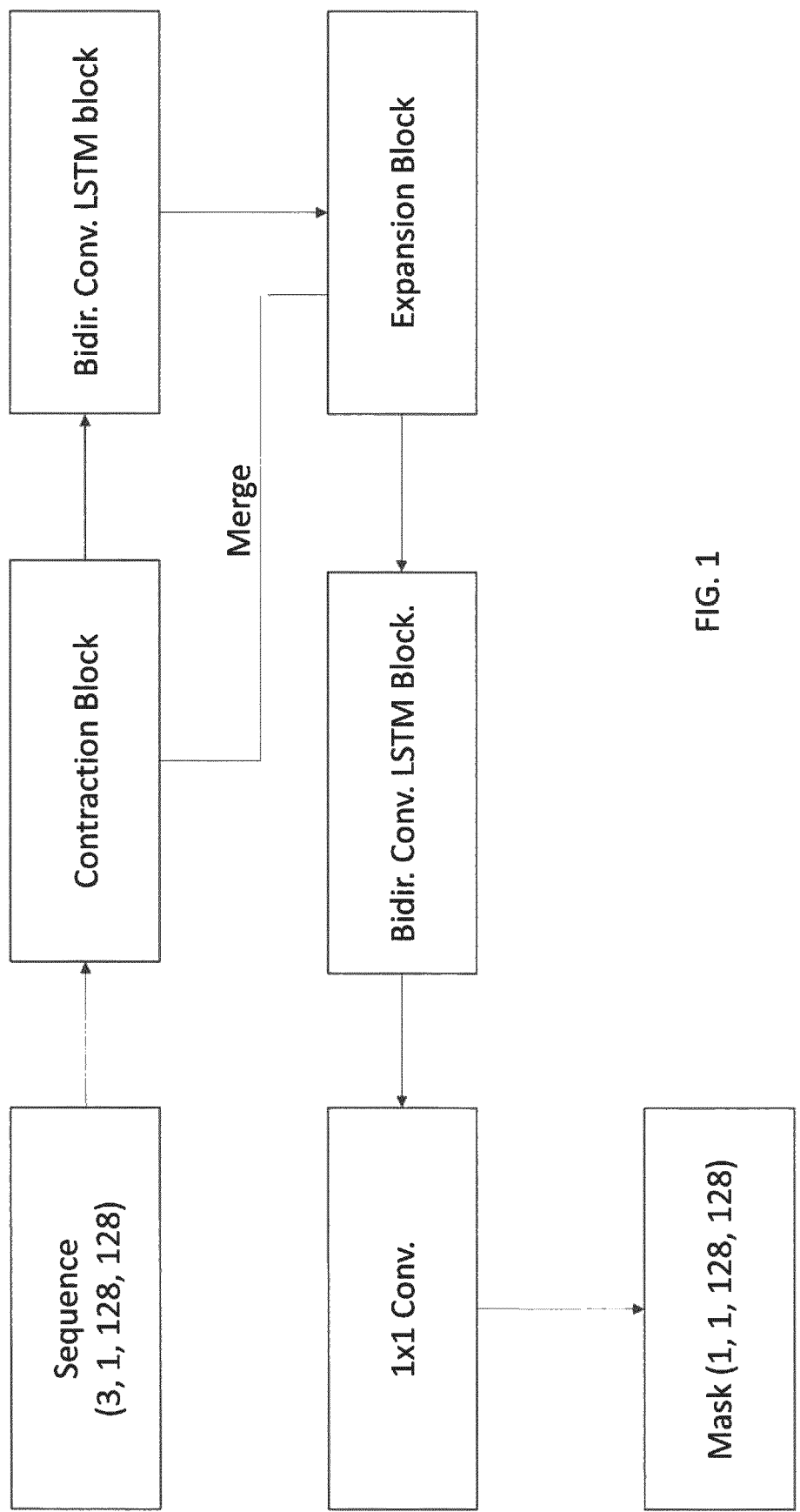

(51) Int. Cl.
*G16H 30/20* (2018.01)
*G06N 3/08* (2023.01)
(52) U.S. Cl.
CPC .............................. *G06T 2200/04* (2013.01); *G06T 2207/20081* (2013.01); *G06T 2207/20084* (2013.01); *G06T 2207/30012* (2013.01); *G06T 2207/30056* (2013.01)
(58) Field of Classification Search
CPC ........... G06T 2207/30012; G06T 2207/30056; G06N 3/08; G16H 30/20
USPC ......................................................... 382/131
See application file for complete search history.

(56) References Cited

U.S. PATENT DOCUMENTS

| | | | | |
|---|---|---|---|---|
| 2019/0021677 | A1* | 1/2019 | Grbic | G06T 7/11 |
| 2019/0205606 | A1* | 7/2019 | Zhou | G06V 20/695 |
| 2019/0223725 | A1* | 7/2019 | Lu | G06N 3/044 |
| 2021/0241884 | A1* | 8/2021 | Swisher | G06V 10/82 |

OTHER PUBLICATIONS

International Search Report dated Jun. 21, 2019 relating to PCT/EP2019/063745, 3 pages.
Written Opinion dated Jun. 21, 2019 relating to PCT/EP2019/063745, 6 pages.
Avinash Sharma V, "Understanding Activation Functions in Neural Networks", The Theory of Everything, Mar. 30, 2017, https://medium.com/the-theory-of-everything/understandingactivation-functions-in-neural-networks-9491262884e0.
Chen Yani et al, "Accurate and Consistent Hippocampus Segmentation Through Convolutional LSTM and View Ensemble", International Workshop on Machine Learning in Medical Imaging, Sep. 7, 2017, pp. 88-96, Lecture Notes in Computer Science vol. 10541, Springer, Cham.
Olaf Ronneberger et al., "U-Net: Convolutional Networks for Biomedical Image Segmentation", Medical Image Computing and Computer-Assisted Intervention, Lecture Notes in Computer Science vol. 935, May 18, 2015, pp. 234-241, Springer, Cham.

* cited by examiner

| Layer Name | Layer Type | Input Shape | Filters | Output Shape |
|---|---|---|---|---|
| conv_1 | TD-Conv | 3x1x128x128 | 3x64x3x3 | 3x64x128x128 |
| conv_2 | TD-Conv | 3x64x128x128 | 3x64x3x3 | 3x64x128x128 |
| pool_1 | TD-MaxP | 3x64x128x128 | 3x2x2 | 3x64x64x64 |
| conv_4 | TD-Conv | 3x64x64x64 | 3x128x3x3 | 3x128x64x64 |
| conv_5 | TD-Conv | 3x128x64x64 | 3x128x3x3 | 3x128x64x64 |
| pool_2 | TD-MaxP | 3x128x64x64 | 3x2x2 | 3x128x32x32 |
| conv_7 | TD-Conv | 3x256x32x32 | 3x256x3x3 | 3x256x32x32 |
| conv_8 | TD-Conv | 3x256x32x32 | 3x256x3x3 | 3x256x32x32 |
| pool_3 | TD-MaxP | 3x256x32x32 | 3x2x2 | 3x256x16x16 |
| bidir_1 | Bidir ConvLSTM | 3x256x16x16 | 512x3x3 | 3x512x16x16 |
| up_1 | TD-Ups | 3x512x16x16 | 3x2x2 | 3x512x32x32 |
| concat_1 | Conc(conv8, up_1) | | | 3x768x32x32 |
| conv_11 | TD-Conv | 3x768x32x32 | 256x3x3 | 3x256x32x32 |
| conv_12 | TD-Conv | 3x256x32x32 | 256x3x3 | 3x256x32x32 |
| up_2 | TD-Ups | 3x256x32x32 | 3x2x2 | 3x256x64x64 |
| concat_2 | Conc(conv5,up_2) | | | 3x384x64x64 |
| conv_14 | TD-Conv | 3x384x64x64 | 128x3x3 | 3x128x64x64 |
| conv_15 | TD-Conv | 3x128x64x64 | 128x3x3 | 3x128x64x64 |
| up_3 | TD-Ups | 3x128x64x64 | 3x2x2 | 3x128x128x128 |
| concat_3 | Conc(conv-,up_3) | | | 3x192x128x128 |
| conv_17 | TD-Conv | 3x192x128x128 | 64x3x3 | 3x64x128x128 |
| bidir_2 | Bidir ConvLSTM | 3x64x128x128 | 64x3x3 | 1x64x128x128 |
| conv_output | Convolution 2D | 1x64x128x128 | 1x1x1 | 1x1x128x128 |

FIG. 2

| Anatomical organ | Vertebrae (full volume) | | Liver (full volume) | | Vertebrae (organ area) | | Liver (organ area) | |
| --- | --- | --- | --- | --- | --- | --- | --- | --- |
| Metrics | D | J | D | J | D | J | D | J |
| Fold 1 | 0.942 | 0.890 | 0.928 | 0.867 | 0.961 | 0.924 | 0.948 | 0.901 |
| Fold 2 | 0.919 | 0.850 | 0.950 | 0.906 | 0.940 | 0.887 | 0.954 | 0.912 |

FIG. 3

SEQUENTIAL SEGMENTATION OF ANATOMICAL STRUCTURES IN 3D SCANS

CROSS-REFERENCE TO RELATED APPLICATIONS

This application is a 371 National Stage Application of PCT/EP2019/063745, filed May 28, 2019, which claims the benefit of European Application No. 18176521.5, filed Jun. 7, 2018, the contents of which are incorporated by reference herein in their entirety.

FIELD OF THE INVENTION

The present invention relates to a method of segmenting anatomical structures in volumetric scans, more specifically in medical 3D scans.

Background of the Invention

Accurate segmentation of anatomical structures in volumetric medical scans is of high interest in current clinical practice as it plays an important role in many tasks involved in computer-aided diagnosis, image-guided interventions, radio-therapy and radiology. In particular, quantitative diagnostics requires knowledge of accurate boundaries of anatomical organs.

3D deep learning segmentation approaches show promising results on various organs and modalities. Like the work of Lu et al. [11] on liver segmentation, most of these methods are built upon the 3D U-Net architecture [5]. Dou et al. [6] presented a 3D fully-convolutional architecture which boosts liver segmentation accuracy by deep supervision layers. Yang et al. [16] used adversarial training in order to gain more performance for the 3D U-Net segmentation of the liver in CT scans. Sekuboyina et al. [14] proposed a pipeline approach for both localization and segmentation of the spine in CT. Here the vertebrae segmentation is performed in a blockwise manner to overcome memory limitations and at the same time obtain a fine-grained result. A similar blockwise approach in combination with a multi-scale two-way CNN was introduced by Korez et al. [9].

Aforementioned methods resample scans originating from 3D image acquisition into volumes and apply convolutions in 3D. This involves usually downscaling in order to overcome memory limitations. Therefore, methods that process volumetric data in a slice-wise fashion gained importance. For instance, Li et al. [10] applied first a slice-wise densely connected variant of the U-Net [13] architecture for liver segmentation and refined the result by a 3D model using the auto-context algorithm. For the same task, Christ et al. [4] applied slice-wise U-Nets to obtain a rough segmentation and refined the result with Conditional Random Fields in 3D.

For proper leveraging spatial information, relying only on intra-slice data is insufficient. Addressing this issue, the above-mentioned methods applied computationally expensive 3D refinement strategies in addition to the main 2D approach.

On contrary, Bates et al. [2] and Chen et al. [3] show that combining recurrent neural networks with 2D fully convolutional approaches allows to process spatial information over slices directly. The presented methods use a U-Net variant to yield an initial segmentation, which subsequently is refined by convolutional Long Short Term Memory Networks (LSTMs) [7].

It is an aspect of the present invention to provide an improved segmentation method.

SUMMARY OF THE INVENTION

The above-mentioned aspects are realized by a method as set out in claim 1.

Specific features for preferred embodiments of the invention are set out in the dependent claims.

The method of this invention is a general, robust, end-to-end hybrid of the U-Net, time-distributed convolutions and bidirectional convolutional LSTM blocks.

The method overcomes disadvantages of current methods such as disregarding anisotropic voxel sizes, considering only intra-slice information, and memory constraints.

Furthermore, invariance to field-of-view is shown, especially to constant slice count by evaluating on two CT datasets depicting two different organs, namely liver and vertebrae. Liver segmentation is often a required step in the diagnosis of hepatic diseases while the segmentation of vertebrae is important for the identification of spine abnormalities, e.g. fractures, or image-guided spine intervention.

Further advantages and embodiments of the present invention will become apparent from the following description and drawings.

BRIEF DESCRIPTION OF THE D WINGS

FIG. 1 shows an overview of the architecture underlying the method of the present invention, FIG. 2 is a table with detailed information on filters and shapes for input and output tensors, FIG. 3 are the results of two-fold evaluations on vertebrae and liver,

DETAILED DESCRIPTION OF THE INVENTION

Methodology

General Setup

Let $I=\{I_1, \ldots, I_n\}$ a set of volumetric scans, where each $I_i$ consists of voxels $(x_1,x_2,x_3) \in \mathcal{R}^3$ and intensities $I_i(x) \in J \subset \mathcal{R}$.

More specifically, each scan $I_i$ is therefore a set of $m_{I_i} \in N$ slices $$J_{I_i} = \{J_1, \ldots J_{m_{I_i}}\}$$

with pixels $y=(y_1,y_2) \in \mathcal{R}^2$ and intensities $J_{I_i}(y) \in J$.

For each slice $J_i \in J_{I_i}$ a set of ground truth masks are available $$M_{J_i} = M_{J_i,l})_{l=1}^m$$

where l corresponds to semantic class labels $\mathcal{L}=\{l_1 \ldots l_m\}$ and $M_{J_i} \in \mathcal{M} \subset M^{m_1 \times m_2}(\{0,1\})$, the space of all binary matrices of size $m_1 \times m_2$.

To enforce reproducibility of the input flow shapes, a new training dataset was built in the following way.

From each scan $I_i \in I$ a subset $J_{I_i}' \subset J_{I_i}$ of size $k_{J_i}$ is selected where $k_{J_i}$ is dividable by an odd number $O_{J_i} \in N$.

Subsequently, each $J_{I_i}'$ is split into order-preserving subsets of the length $O_{J_i}$, and all are combined into a new dataset I' that now consists of the subsets of odd cardinality.

For training and evaluation purposes, the dataset I' is split into non-overlapping sets, namely $I_{Train}'$ and $I_{Test}'$.

During training the network is consecutively passed with minibatches $\mathcal{K} \in \mathcal{N}$, where $\mathcal{N}$ is a complete partition of the set $I_{Train}'$.

For each sequence $I_j' \in I'$, i.e. $I_j'=\{J_p, \ldots J_q\}$ for some $1 \leq p,q \leq |J_{I_i}|$ and some sequence $I_i$, the multi-class output of the network is calculated:

understanding the network as a function $\mathcal{N} : I' \rightarrow \mathcal{M}$ (1)

$\mathcal{N}(I_j')$ derives for each pixel $y \in J_p$ its semantic class $l \in \mathcal{L}$ in a single step with some probability, where $J_p$ corresponds to the middle element of the sequence $I_j'$.

In order to estimate and maximize this probability, a loss function is defined as follows $\Lambda: I' \times \mathcal{M} \rightarrow \mathcal{R}$ (2)

that estimates the deviation (error) of the network outcome from the desired ground truth.

Using the formal notations derived by Novikov et al. [12] a loss function is defined in the following way.

For a distance function $d: I' \times \mathcal{M} \rightarrow \mathcal{R}$, weighting coefficients $\tau_{\kappa,l}$ and a sequence $S \in K$ the loss function is $\Lambda(S,G_S) := -\Sigma_{l \in \mathcal{L}} r_{\kappa,l}^{-1} d_l^{dice}(S, G_S)$ (3)

over the set K and the complete partition.

The distance function $d_l^{dice}$ for the Dice coefficient for a training sequence S, a feature channel l, ground-truth mask $G_S$ and sigmoid activation function $p_l(.)$ can be defined as $$d_l^{dice}(S, G_S) := 2 \frac{\Sigma_{x \in I} X_{\pi_l(G_S)}(x) p_l(x)}{\Sigma_{x \in I} (X_{\pi_l(G_S)}(x) + p_l(x))}$$

Where $X_{\pi_l(G_S)}(x)$ is a characteristic function, i.e. $X_{\pi_l(G_S)}(x)=1$ if $G_S$ is 1 at the position of pixel x and 0 otherwise.

Architecture

In order to leverage spatio-temporal correlations of the order-preserving slices (elements of $I_j'$) and due to their sequential nature, time-distributed convolutions and bidirectional convolutional LSTM blocks have been combined in an end-to-end trainable U-Net-like hybrid architecture.

FIG. 1 shows a high-level overview of the proposed architecture.

FIG. 2 complements FIG. 1 with tensor shapes for each layer.

The network takes an odd-lengthed sequence $J_i \in I_j'$ as the input.

This sequence is then passed to a contraction block. Each element of the sequence is processed through the contraction block of the network independently. The contraction block consists of the repeated time-distributed convolution and max-pooling layers.

Time-distributed convolutions are typical convolutions passed to a special wrapper. Time-distributed wrappers allow application of any layer to every temporal frame (or slice) of the input independently. In the context of this work such temporal frames correspond to the elements of the training sequences extracted from the volumes. In the present architecture the wrapper is applied in all convolutional, pooling, upsampling and concatenation layers.

In order to capture spatio-temporal correlations between slices the features extracted for each element of the input sequence have been passed into a Convolutional LSTM (CLSTM) block [15] at the end of the contraction part of the network.

A bidirectional modification of the CLSTM is used with a summation operator in order to enable the network learning spatio-temporal correlations of the slices in both directions.

This CLSTM block aims at adding the dependency of the low-dimensional high abstract features.

The sequence output of the bidirectional CLSTM block is then passed to the expansion path. Each element of the sequence is processed independently.

The expansion part consists of the time-distributed convolutions and up-sampling layers. After every up-sampling layer, the features are concatenated with the corresponding features from the contraction part. When the spatial resolution of the features reaches the desired sizes, the sequence is passed to another bidirectional CLSTM block. The sequence is processed in both directions and the output is summed. Therefore this block contributes towards two goals: adding dependency for the high-dimensional features and converting the incoming sequence into a single-channeled output.

The resulting features are then passed to the (1,1) convolution layer in order to map each feature vector to the desired number of classes. The result is mapped into [0,1] range via the sigmoid activation applied to each pixel independently. This results in the segmentation of the middle element of the input sequence $J_i$.

Experimental Setup

Training Data and Preparation

To demonstrate the generalizability of this architecture on different anatomical organs public datasets were used for vertebrae and liver.

For vertebrae segmentation the CSI 2014 challenge train set [17] was used. It comprises of 10 CT scans covering the entire lumbar and thoracic spine and full vertebrae segmentation masks for each scan. The axial in-plane resolution varies between 0.3125 and 0.3616 mm2 and the slice thickness is 1 mm.

For liver segmentation the following two related datasets were used: 3Dircadb-01 and 3Dircadb-02 [1]. The first consists of 20 3D CT scans of 10 and 10 men with hepatic tumours in 75% cases. The second one consists of two anonymized scans with hepatic focal nodular hyperplasia. The axial in-plane resolution varied between 0.56 and 0.961 $mm^{-2}$ and the slice thickness varied between 1.0 and 4.0 mm.

The consecutive elements within the training sequences for the vertebrae segmentation were generated at the distance of 3 mms and at 5 mms for liver segmentation within the vertebrae and liver areas.

These numbers were chosen based on the maximal slice thicknesses in the datasets. In all evaluations we used the sequences of three slices ($oJ_i==3, \forall J_i \in_j'$).

Evaluations on both organs were performed in a two-fold manner. All slices and masks were downsampled to 128×128 imaging resolution for timely evaluation runs.

Implementation Details

All experiments were performed using Keras with TensorFlow backend in Python. We trained the networks over the loss shown by Eq. 3 using an ADAM [8] optimization algorithm with a fixed initial rate of 10-5 and the standard values of $\beta1=0.9$ and $\beta2=0.999$. Downsampling of the ground-truth masks was performed using the scikit-image library.

Results

The average Dice and Jaccard scores for two folds for vertebrae and liver segmentation are shown in FIG. 3. The first two columns show the scores for the case when the whole volume was considered, even when the organ of interest was not present. The third and fourth columns show the results only for the regions containing the organ of interest.

The focus of this invention is on the general segmentation approach therefore the final result is not post-processed because usually this procedure is task-specific and requires organ-specific tuning. In this case, as expected, for this context irrelevant bone structures were partially segmented thus lowering the scores for the full volume.

In order to demonstrate that the present network improves over its 2D variations, two more architectures were built and evaluated in the same training conditions on the Fold 1 for liver.

In the first architecture the input was changed in a way that it would take the sequences consisting of only one slice (the middle slice we aimed to segment).

In the second architecture the input dimensions were not changed but the first convolutional LSTM block was removed and replaced the second one by the aggregation layer which would sum the incoming features over the time channel.

Both architectures achieved similar Dice scores of 0.87 and 0.878 when considering the organ area only, which is significantly lower than the scores of the network of this invention.

REFERENCES 1. 3d-ircadb database. Available at https://www.ircad.fr/research/3d-ircadb-01/.
2. R. Bates, B. Irving, B. Markelc, J. Kaeppler, R. Muschel, V. Grau, and J. A. Schnabel. Extracting 3D vascular structures from microscopy images using convolutional recurrent networks. arXiv preprint arXiv:1705.09597, 2017.
3. J. Chen, L. Yang, Y. Zhang, M. Alber, and D. Z. Chen. Combining fully convolutional and recurrent neural networks for 3D biomedical image segmentation. In NIPS, pages 3036-3044, 2016.
4. P. F. Christ, M. E. A. Elshaer, F. Ettlinger, S. Tatavarty, Bickel, P. Bilic, M. Rempfler, M. Armbruster, F. Hofmann, M. DAnastasi, et al. Automatic liver and lesion segmentation in CT using cascaded fully convolutional neural networks and 3D conditional random fields. In MICCAI, pages 415-423. Springer, 2016.
5. Ö Cicek, A. Abdulkadir, S. S. Lienkamp, T. Brox, and O. Ronneberger. 3D U-Net: Learning dense volumetric segmentation from sparse annotation. In MICCAI, pages 424-432, Cham, 2016. Springer International Publishing.
6. Q. Dou, H. Chen, Y. Jin, L. Yu, J. Qin, and P.-A. Heng. 3D deeply supervised network for automatic liver segmentation from CT volumes. In MICCAI, pages 149-157. Springer, 2016.
7. S. Hochreiter and J. Schmidhuber. Long short-term memory. Neural computation, 9(8):1735-1780, 1997.
8. D. Kingma and J. Ba. Adam: A method for stochastic optimization. ICLR, 2015.
9. R. Korez, B. Likar, F. Pernǔs, and T. Vrtovec. Segmentation of pathological spines in CT images using a two-way CNN and a collision-based model. In International Workshop and Challenge on Computational Methods and Clinical Applications in Musculoskeletal Imaging, pages 95-107. Springer, 2017.
10. X. Li, H. Chen, X. Qi, Q. Dou, C.-W. Fu, and P. A. Heng. H-DenseUNet: Hybrid densely connected U-Net for liver and liver tumor segmentation from CT volumes. arXiv preprint arXiv:1709.07330, 2017.
11. F. Lu, F. Wu, P. Hu, Z. Peng, and D. Kong. Automatic 3D liver location and segmentation via convolutional neural network and graph cut. International Journal of CARS, 12(2):171-182, 2017.
12. A. A. Novikov, D. Lenis, D. Major, J. Hlaďuvka, M. Wimmer, and K. Bühler. Fully convolutional architectures for multi-class segmentation in chest radiographs. IEEE Transactions on Medical Imaging, PP(99):1-1, 2018.
13. O. Ronneberger, P. Fischer, and T. Brox. U-Net: Convolutional networks for biomedical image segmentation. In MICCAI, pages 234-241. Springer, 2015.
14. A. Sekuboyina, J. Kukacka, J. S. Kirschke, B. H. Menze, and A. Valentinitsch. Attention-driven deep learning for pathological spine segmentation. In International Workshop and Challenge on Computational Methods and Clinical Applications in Musculoskeletal Imaging, pages 108-119. Springer, 2017.
15. X. Shi, Z. Chen, H. Wang, D.-Y. Yeung, W.-k. Wong, and W.-c. Woo. Convolutional LSTM network: A machine learning approach for precipitation nowcasting. In NIPS, NIPS, pages 802-810. MIT Press, 2015.
16. D. Yang, D. Xu, S. K. Zhou, B. Georgescu, M. Chen, S. Grbic, D. Metaxas, and D. Comaniciu. Automatic liver segmentation using an adversarial image-to-image network. In MICCAI, pages 507-515. Springer, 2017.
17. J. Yao, J. E. Burns, H. Munoz, and R. M. Summers. Detection of vertebral body fractures based on cortical shell unwrapping. In MICCAI, pages 509-516, Berlin, Heidelberg, 2012. Springer Berlin Heidelberg.

Having described in detail preferred embodiments of the current invention, it will now be apparent to those skilled in the art that numerous modifications can be made therein without departing from the scope of the invention as defined in the appending claims.

The invention claimed is:

1. A computer-implemented method of segmenting anatomical structures in a three-dimensional (3D) medical image representation by applying a trained neural network comprising:
   selecting an odd length sequence of two-dimensional (2D) slices, said 2D slices derived from said 3D medical image representation,
   passing said sequence through a contraction block, said contraction block comprising a number of repeated time-distributed convolution and max-pooling layers,
   feeding an output of the contraction block for each of the 2D slices of said sequence to a first bidirectional convolutional Long Short Term Memory (LSTM) block, said first bidirectional convolutional LSTM block configured to extract processed features which are similar from the output of the contraction block,
   passing an output of said first bidirectional convolutional LSTM block to an expansion block, said expansion block comprising a number of time-distributed convolution and upsampling layers, said expansion block being arranged to concatenate features input to said expansion block with corresponding features output by said contraction block,
   passing a sequence of concatenated features output by said expansion block to a second bidirectional convolutional LSTM block when a spatial resolution of the sequence of concatenated features reaches a preset size,
      wherein the sequence of concatenated features is processed bi-directionally by the second bidirectional convolutional LSTM block and an output thereof is combined, applying features resulting from the second bidirectional convolutional LSTM block to a (1,1) convolutional layer, and subjecting each pixel resulting from application of said (1,1) convolutional layer individually to an actuation by a sigmoid function so as to obtain a mask between (0,1) resulting in a segmentation mask of a middle element of said odd length sequence.

2. The computer-implemented method of claim 1, further comprising:

splitting the odd length sequence into a training set and a test set, wherein the anatomical structures of the training set and the anatomical structures of the test set do not overlap; and training the neural network with the training set.

3. The computer-implemented method of claim 1, wherein passing the sequence through the contraction block comprises processing each of the 2D slices of the sequence independently.

4. The computer-implemented method of claim 1, wherein the bi-directionally processed concatenated features output by the second bidirectional convolutional LSTM block are combined by summing.

5. The computer-implemented method of claim 1, wherein the second bidirectional convolutional LSTM block is configured to convert the sequence of concatenated features input thereto into a single-channel output.

6. The computer-implemented method of claim 5, wherein applying the features resulting from the second bidirectional convolutional LSTM block to the (1,1) convolutional layer comprises mapping the single-channel output of the second bidirectional convolutional LSTM block to a desired number of classes.

7. The computer-implemented method of claim 1, wherein the first bidirectional convolutional LSTM block is further configured to capture spatio-temporal correlations between the 2D slices.

8. A trained neural network for segmenting anatomical structures in a three-dimensional (3D) medical image representation comprising:

computer-executable instructions that, when executed by a computing device, configure the computing device to:
select an odd length sequence of two-dimensional (2D) slices, the 2D slices derived from the 3D medical image representation,
input the odd length sequence to a contraction block, the contraction block configured to perform a plurality of repeated time-distributed convolution and max-pooling layers on the odd length sequence,
input an output of the contraction block for each of the 2D slices of the odd length sequence to a first bidirectional convolutional Long Short Term Memory (LSTM) block, the first bidirectional convolutional LSTM block configured to extract processed features that are similar to each other from the output of the contraction block,
input an output of the first bidirectional convolutional LSTM block to an expansion block, the expansion block comprising a number of time-distributed convolution and upsampling layers, the expansion block configured to concatenate features input to the expansion block with corresponding features output by the contraction block,
input a sequence of concatenated features output by the expansion block to a second bidirectional convolutional LSTM block when a spatial resolution of the sequence of concatenated features reaches a preset size, the second bidirectional convolutional LSTM block configured to process the sequence of concatenated features bi-directionally and to combine an output thereof,
apply an output of the second bidirectional convolutional LSTM block to a (1,1) convolutional layer, and
subject each pixel resulting from application of the (1,1) convolutional layer individually to an actuation by a sigmoid function so as to obtain a mask between (0,1),
wherein the mask comprises a segmentation mask of a middle element of the odd length sequence.

9. The trained neural network of claim 8, wherein the computer-executable instructions, when executed by the computing device, further configure the computing device to:

split the odd length sequence into a training set and a test set, wherein the anatomical structures of the training set and the anatomical structures of the test set do not overlap; and train the neural network with the training set.

10. The trained neural network of claim 8, wherein the contraction block is configured to process each of the 2D slices of the sequence independently.

11. The trained neural network of claim 8, wherein the bi-directionally processed concatenated features output by the second bidirectional convolutional LSTM block are combined by summing.

12. The trained neural network of claim 8, wherein the second bidirectional convolutional LSTM block is further configured to convert the sequence of concatenated features input thereto into a single-channel output.

13. The trained neural network of claim 12, wherein the (1,1) convolutional layer is configured to map the single-channel output of the second bidirectional convolutional LSTM block to a desired number of classes.

14. The trained neural network of claim 8, wherein the first bidirectional convolutional LSTM block is further configured to capture spatio-temporal correlations between the 2D slices.

15. A system for processing anatomical structures in a three-dimensional (3D) medical image representation comprising:

a segmentation processor; and
a memory device storing computer-executable instructions that, when executed by the processor, configure the processor to execute a neural network for:
selecting an odd length sequence of two-dimensional (2D) slices, the 2D slices derived from the 3D medical image representation,
executing a contraction block, the contraction block configured to perform a plurality of repeated time-distributed convolution and max-pooling layers on the odd length sequence,
executing a first bidirectional convolutional Long Short Term Memory (LSTM) block, the first bidirectional convolutional LSTM block configured to extract features from an output of the contraction block for each of the 2D slices of the odd length sequence that are similar to each other,
executing an expansion block, the expansion block comprising a number of time-distributed convolution and upsampling layers, the expansion block configured to concatenate features extracted by the first bidirectional convolutional LSTM block with corresponding features output by the contraction block, inputting a sequence of concatenated features output by the expansion block to a second bidirectional convolutional LSTM block when a spatial resolution of the sequence of concatenated features reaches a preset size, the second bidirectional convolutional LSTM block configured to process the sequence of concatenated features bi-directionally and to combine an output thereof, applying an output of the second bidirectional convolutional LSTM block to a (1,1) convolutional layer, and subjecting each pixel resulting from application of the (1,1) convolutional layer individually to an actuation by a sigmoid function so as to obtain a mask between (0,1), wherein the mask comprises a segmentation mask of a middle element of the odd length sequence.

16. The system of claim 15, wherein the computer-executable instructions, when executed by the processor, further configure the processor to:

split the odd length sequence into a training set and a test set, wherein the anatomical structures of the training set and the anatomical structures of the test set do not overlap; and train the neural network with the training set.

17. The system of claim 15, wherein the contraction block is configured to process each of the 2D slices of the sequence independently.

18. The system of claim 15, wherein the bi-directionally processed concatenated features output by the second bidirectional convolutional LSTM block are combined by summing.

19. The system of claim 15, wherein the second bidirectional convolutional LSTM block is further configured to convert the sequence of concatenated features input thereto into a single-channel output.

20. The system of claim 15, wherein the first bidirectional convolutional LSTM block is further configured to capture spatio-temporal correlations between the 2D slices.

* * * * *